(12) United States Patent
Zhu et al.

(10) Patent No.: US 11,331,405 B2
(45) Date of Patent: May 17, 2022

(54) ELECTRONICALLY-ACTIVATED, SELF-MOLDING AND RE-SHAPEABLE LOAD-BEARING SUPPORT STRUCTURE SYSTEM AND METHODS FOR MOLDING THEREOF

(71) Applicant: Nano and Advanced Materials Institute Limited, Hong Kong (HK)

(72) Inventors: Yong Zhu, Hong Kong (HK); Cheuk Yin Lee, Hong Kong (HK); Chenmin Liu, Hong Kong (HK); Shengbo Lu, Hong Kong (HK)

(73) Assignee: Nano and Advanced Materials Institute Limited, Hong Kong (HK)

( * ) Notice: Subject to any disclaimer, the term of this patent is extended or adjusted under 35 U.S.C. 154(b) by 386 days.

(21) Appl. No.: 16/579,837

(22) Filed: Sep. 24, 2019

(65) Prior Publication Data
US 2020/0101190 A1   Apr. 2, 2020

Related U.S. Application Data

(60) Provisional application No. 62/919,614, filed on Mar. 22, 2019, provisional application No. 62/766,042, filed on Sep. 28, 2018.

(51) Int. Cl.
*A61F 5/00* (2006.01)
*A61L 15/14* (2006.01)
(Continued)

(52) U.S. Cl.
CPC ............. *A61L 15/14* (2013.01); *A61L 15/125* (2013.01); *A61D 9/00* (2013.01)

(58) Field of Classification Search
CPC .......... A61F 5/058; A61F 5/371; A61L 15/07; A61L 15/125; A61L 15/14; B29C 51/421; A61D 9/00; B29K 2067/046
(Continued)

(56) References Cited

U.S. PATENT DOCUMENTS

| 3,326,211 A * | 6/1967 | Logue ............... A61F 13/04 602/7 |
| 2008/0262400 A1 | 10/2008 | Clark et al. |
| 2013/0102940 A1 | 4/2013 | Joseph |

FOREIGN PATENT DOCUMENTS

| CN | 1502313 A | 6/2004 |
| CN | 106102666 A | 11/2016 |

(Continued)

OTHER PUBLICATIONS

First Office Action of Corresponding China Invention Patent Application No. 201910912572.X dated Jun. 25, 2021.

*Primary Examiner* — Kim M Lewis
(74) *Attorney, Agent, or Firm* — Idea Intellectual Limited; Margaret A. Burke; Sam T. Yip

(57) ABSTRACT

An electronically-activated, self-molding and re-shapeable load-bearing support structure system is provided that includes a first composite structure. The first composite structure includes a first layer of a first thermally-responsive polymer; one or more first heating elements positioned adjacent to the first layer on a first heating element side; a second layer of the first thermally-responsive polymer positioned adjacent to the first heating elements on a second heating element side; a temperature sensor communicating with at least the first layer or the second layer of the first thermally-responsive polymer; one or more electrical connectors electrically communicating with the heating elements; and an electrical controller detachably connectable to at least one of the electrical connectors of the composite for providing an electrical current to the heating elements. A method of molding the load-bearing support structure system is also provided.

17 Claims, 5 Drawing Sheets

(51) Int. Cl.
 *A61L 15/12* (2006.01)
 *A61D 9/00* (2006.01)
(58) Field of Classification Search
 USPC .............................................. 602/7
 See application file for complete search history.

(56) References Cited

FOREIGN PATENT DOCUMENTS

| | | | |
|---|---|---|---|
| CN | 106840476 | A | 6/2017 |
| CN | 206228482 | U | 6/2017 |
| JP | 2002048053 | A | 2/2002 |

\* cited by examiner

ELECTRONICALLY-ACTIVATED, SELF-MOLDING AND RE-SHAPEABLE LOAD-BEARING SUPPORT STRUCTURE SYSTEM AND METHODS FOR MOLDING THEREOF

CROSS-REFERENCE TO RELATED APPLICATION

The present application claims the priorities from the U.S. provisional patent application Ser. No. 62/766,042 filed Sep. 28, 2018 and the U.S. provisional patent application Ser. No. 62/919,614 filed Mar. 22, 2019, and the disclosures of which are incorporated herein by reference in their entirety.

FIELD OF THE INVENTION

The present invention relates to load-bearing support structure systems, methods for molding the load-bearing support structure system, and applications thereof on orthopaedic fixation, fracture fixing device, orthopaedic immobilization, radiation fixation, therapeutic fixation, electro-controlled wrist band/watch band, electro-controlled transformable supporting pad/plate or related products, etc.

BACKGROUND

Fixation is commonly used in medical application, especially for healing broken bones, rehabilitation therapy, orthopaedic cure and limb/head fixation during therapy radiation. Traditional fixing methods such as wood splint and plaster external fixation are widely used. However, traditional fixing methods have some disadvantages to the patients, such as (i) splints made from wood have the disadvantage of a lack of good molding property and the potential to cause pressure sores, (ii) plaster external fixation may affect the blood circulation at the distal end and has poor permeability. Therefore, different fixing methods have been developed in response to these shortcomings.

Thermoplastics are polymers which become soft and flow upon heating, and then become hard again when cooled. In recent years, thermoplastic plate becomes more popular for its convenience in usage through hot water to soften the plate and the good fitting performance in hot status.

US586797 discloses a method for preparing a thermoplastic material, with dry heat, for use in patient fixation. The method includes generating heat to a threshold temperature and transferring the heat to the thermoplastic material by a heat conductive path. Once the thermoplastic material has become pliable, it is molded into a cast for fixation purposes.

EP2537882B1 discloses a thermoplastic sheet comprising a thermoplastic composition for forming a cast such as a radiation mask, the composition having a polymeric component comprising a mixture of a styrene acrylonitrile copolymer and poly-caprolactone, optionally together with a cross-linker and/or a filler.

U.S. Pat. No. 9,950,191B2 discloses a system for immobilization of a patient body part for radiotherapy applications which includes a device having at least one flanged support member which is suitable to be mounted to a fixation surface and is adapted to receive and retain at least two sheets is described. The first sheet covers the anatomical contours of a first area of the body part, and the second sheet covers the anatomical contours of a second area of the body part which is not covered by the first sheet. The system is capable of supporting the immobilized body part by the two sheets and the device.

CN1669590A discloses an antibacterial shape memory polyurethane for orthopedic, fixing and rehabilitative plate and preparation method, where the sheet material comprises shape memory polyurethane 95-75 weight parts, antibacterial agent 1.5-3 weight parts, and mineral filler 5-25 weight parts.

However, all the thermoplastic materials need to be softened by heating through an external heating element or device, and the operation time to use such soft material after heating is quite limited. It is hard to control the hardening time according to patient's actual need. In addition, some types of low-quality thermoplastic compositions may melt when they are exposed to ultraviolet light for extended times, and thermoplastics compositions have poor resistance to organic solvents, hydrocarbons and highly polar solvents.

In view of the disadvantages of the existing thermoplastic compositions, it is necessary to develop another fast hardening, fast softening, and safer material for fixation application.

SUMMARY OF THE INVENTION

Accordingly, an objective of this invention is to provide an electronically-activated, self-molding and re-shapeable load-bearing support structure system for healing broken bones, rehabilitation therapy, orthopaedic cure and body/limb/head fixation during therapy radiation.

In a first aspect of the present invention, an electronically-activated, self-molding and re-shapeable load-bearing support structure system including a first composite structure is provided, which comprises a first layer of a first thermally-responsive polymer having a first elastic modulus at a temperature below a glass transition temperature or a melting temperature and a second elastic modulus at a temperature greater than the glass transition temperature or the melting temperature, when the first elastic modulus is larger than the second elastic modulus by at least approximately 10 to approximately 100 times; one or more first heating elements positioned adjacent to the first layer on a first heating element side, the one or more first heating elements selected from one or more of carbon fibers, carbon fabric, conductive inks, metal mesh, metal film, metal wires, or flexible printed circuits, the one or more first heating elements forming a first heating zone; a second layer of the first thermally-responsive polymer positioned adjacent to the one or more first heating elements on a second heating element side, the second layer having a first elastic modulus at a temperature below a glass transition temperature or a melting temperature and a second elastic modulus at a temperature greater than the glass transition temperature or the melting temperature, when the first elastic modulus is larger than the second elastic modulus by at least approximately 10 to approximately 100 times larger; a temperature sensor communicating with at least the first layer or the second layer of the first thermally-responsive polymer; one or more electrical connectors electrically communicating with the one or more heating elements; and an electrical controller detachably connectable to at least one of the one or more electrical connectors of the composite for providing an electrical current to the one or more heating elements, the electrical controller electrically communicating with the temperature sensor when the electrical controller is connected to the one or more electrical connectors and for providing electricity to the heating element, the amount of electricity being determined by a measured temperature from the temperature sensor and a predetermined set temperature above the glass transition temperature or the melting temperature.

In a first embodiment of the first aspect, the load-bearing support structure system further includes one or more second heating elements positioned between the first layer and the second layer of the first thermally-responsive polymer, the one or more second heating elements selected from one or more of carbon fibers, carbon fabric, conductive inks, metal mesh, metal film, metal wires, or flexible printed circuits, the one or more second heating elements forming a second heating zone, the second heating zone being independently controllable by the controller from the first heating zone.

In a second embodiment of the first aspect, the composite structure further includes a third layer of a second thermally-responsive polymer laterally adjacent to the first layer of the first thermally-responsive polymer having a third elastic modulus at a temperature below a glass transition temperature or a melting temperature and a fourth elastic modulus at a temperature greater than the glass transition temperature or the melting temperature, when the third elastic modulus is larger than the fourth elastic modulus by at least approximately 10 to approximately 100 times larger and where the third layer of a second thermally-responsive polymer has a third elastic modulus that is greater than the first elastic modulus of the first thermally responsive polymer by at least approximately 10 to approximately 100 times; one or more third heating elements positioned adjacent to the third layer on a first heating element side, the one or more first heating elements selected from one or more of carbon fibers, carbon fabric, conductive inks, metal mesh, metal film, metal wires, or flexible printed circuits, the one or more first heating elements forming a third heating zone; and a fourth layer of the second thermally-responsive polymer positioned adjacent to the one or more third heating elements on a third heating element side, the fourth layer having a third elastic modulus at a temperature below a glass transition temperature or a melting temperature and a fourth elastic modulus at a temperature greater than the glass transition temperature or the melting temperature, when the third elastic modulus is larger than the fourth elastic modulus by at least approximately 10 to approximately 100 times such that a region of the third and fourth layers of the second thermally-responsive material provides a region of greater stiffness or rigidity to the composite structure.

In a third embodiment of the first aspect, the temperature sensor includes a thermocouple, a resistance temperature detector, or a thermistor.

In a fourth embodiment of the first aspect, the controller is configured to provide a temperature from 15° C. to 85° C.

In a fifth embodiment of the first aspect, the controller includes a temperature feedback control circuit.

In a sixth embodiment of the first aspect, the temperature feedback control circuit is selected from a dynamic voltage control or a dynamic current control feedback circuit.

In a seventh embodiment of the first aspect, the controller includes a feedback control circuit.

In an eighth embodiment of the first aspect, the first thermally-responsive polymer layer includes a thermally conductive filler in an amount up to 85 weight %.

In a ninth embodiment of the first aspect, the thermally-conductive filler is selected from one or more of boron nitride (BN), silica coated aluminum nitride (SCAN), metal oxides, $SiO_2$, or non-oxide ceramic powders.

In a tenth embodiment of the first aspect, the first thermally-responsive polymer layer is selected from a polyurethane block co-polymer, polylactic acid, polystyrene or polyacrylate.

In eleventh embodiment of the first aspect, the second thermally-responsive polymer layer is selected from a polyurethane block co-polymer, polylactic acid, polystyrene or polyacrylate.

A second aspect of the present invention provides a method of molding a system, which includes (1) heating the first and second layers of first thermally-responsive polymer to a temperature above a glass transition temperature or a melting temperature of the first thermally-responsive polymer; (2) positioning the first and second layers of first thermally-responsive polymer around a first shape; (3) cooling the first and second layers of first thermally-responsive polymer to retain the first shape.

In a first embodiment of the second aspect, the shape is a human or animal body part.

In a second embodiment of the second aspect, the method further includes (1) reheating the first and second layers of first thermally-responsive polymer to a temperature above a glass transition temperature or a melting temperature of the first thermally-responsive polymer; (2) reshaping the first and second layers of first thermally-responsive polymer into a second shape; (3) cooling the first and second layers of first thermally-responsive polymer to retain the second shape.

In a third embodiment of the second aspect, the second shape is different from the first shape.

The load-bearing support structure system provided by the present invention can realize easy operation, convenient adjustment on human body, low power consumption, compatible mass production.

Detail of the load-bearing support structure system is described hereinafter by embodiments and/or examples.

BRIEF DESCRIPTION OF THE DRAWINGS

Embodiments of the present invention are described in more detail hereinafter with reference to the drawings, in which.

DEFINITIONS

Figure 1:
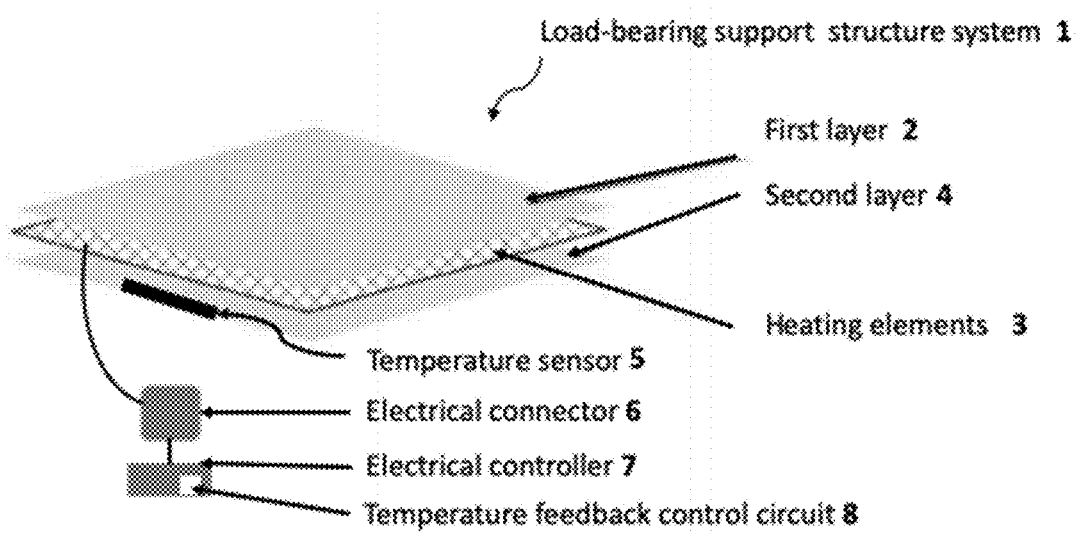
FIG. 1 depicts the configuration of a load-bearing support structure system including a multi-layer composite structure with an electrical controller.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they allow for elements not explicitly recited, but exclude elements that are found in the prior art or that affect a basic or novel characteristic of the present invention.

Furthermore, throughout the specification and claims, unless the context requires otherwise, the word "include" or variations such as "includes" or "including", will be understood to imply the inclusion of a stated integer or group of integers but not the exclusion of any other integer or group of integers.

The terms "a" or "an" are used to include one or more than one and the term "or" is used to refer to a nonexclusive "or" unless otherwise indicated. In addition, it is to be understood that the phraseology or terminology employed herein, and not otherwise defined, is for the purpose of description only and not of limitation. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods of preparation described herein, the steps can be carried out in any order without departing from the principles of the invention, except when a temporal or operational sequence is explicitly recited. Recitation in a claim to the effect that first a step is performed, and then several other steps are subsequently performed, shall be taken to mean that the first step is performed before any of the other steps, but the other steps can be performed in any suitable sequence, unless a sequence is further recited within the other steps. For example, claim elements that recite "Step A, Step B, Step C, Step D, and Step E" shall be construed to mean step A is carried out first, step E is carried out last, and steps B, C, and D can be carried out in any sequence between steps A and E, and that the sequence still falls within the literal scope of the claimed process. A given step or sub-set of steps can also be repeated. Furthermore, specified steps can be carried out concurrently unless explicit claim language recites that they be carried out separately.

References in the specification to "one embodiment", "an embodiment", "an example embodiment", etc., indicate that the embodiment described can include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The terms "glass transition temperature" or "Tg" used herein, or sometimes they are used interchangeably, refer to the temperature at which a glassy substance reversibly transforms between a glassy state and a highly elastic state. In the present invention, the polymer layers possessing Tg in the range between room temperature and 85° C. provides high stiffness when temperature is higher than Tg and low stiffness when temperature is lower than Tg. The modulus change is not less than one order of magnitude when temperature changes across Tg, the first elastic modulus is larger than the second elastic modulus by at least approximately 10 to approximately 100 times; the third elastic modulus is larger than the fourth elastic modulus by at least approximately 10 to approximately 100 times. Sandwiched heating layer inside is used to control the temperature by electrical joule effect.

The terms "melting temperature" or "Tm" used herein, or sometimes they are used interchangeably, refer to the temperature at which a solid, given sufficient heat, becomes a liquid. In the present invention, the polymer layers possessing Tm in the range between room temperature and 85° C. provides high stiffness when temperature is higher than Tm and low stiffness when temperature is lower than Tm. The modulus change is not less than one order of magnitude when temperature changes across Tm, the first elastic modulus is larger than the second elastic modulus by at least approximately 10 to approximately 100 times; the third elastic modulus is larger than the fourth elastic modulus by at least approximately 10 to approximately 100 times. Sandwiched heating layer inside is used to control the temperature by electrical joule effect.

The terms "shape memory polymer (SMP)" or "shape-memory polymeric component" used herein, or sometimes they are used interchangeably, refer to the stimuli-responsive materials that can be deformed and subsequently fixed into a temporary shape. Upon receiving an external stimulus (e.g. heat, solvent, electrical current, light, magnetic field, or change of pH a thermal stimulus), the material will return to its permanent configuration, and then relax to the original, stress-free condition under specific condition. That is, SMPs give materials great potential for application in sensors, actuators, smart devices, and media recorders. Examples of shape memory polymers used in the present invention include, but are not limited to, polyester-based or polyether-based shape memory polyurethane, where polyester-based SMP includes but not limited to polycaprolactone-based SMP.

Other definitions for selected terms used herein may be found within the detailed description of the present invention and apply throughout. Unless otherwise defined, all other technical terms used herein have the same meaning as commonly understood to one of ordinary skill in the art to which the present invention belongs.

Other aspects and advantages of the present invention will be apparent to those skilled in the art from a review of the ensuing description.

DETAILED DESCRIPTION

In the following description, the present load-bearing support structure system and the method for molding the load-bearing support structure system are set forth as preferred examples. It will be apparent to those skilled in the art that modifications, including additions and/or substitutions may be made without departing from the scope and the spirit of the invention, as set forth in the appended claims. Specific details may be omitted so as not to obscure the invention; however, the disclosure is written to enable one skilled in the art to practice the teachings herein without undue experimentation.

An electronically-activated, self-molding and re-shapeable load-bearing support structure system is provided, which includes a first composite structure which comprises a first layer of a first thermally-responsive polymer; one or more first heating elements positioned adjacent to the first layer on a first heating element side; a second layer of the first thermally-responsive polymer positioned adjacent to the one or more first heating elements on a second heating element side; a temperature sensor communicating with at least the first layer or the second layer of the first thermally-responsive polymer; one or more electrical connectors electrically communicating with the one or more heating elements; and an electrical controller detachably connectable to at least one of the one or more electrical connectors of the composite for providing an electrical current to the one or more heating elements. A method of molding the load-bearing support structure system is also provided.

In accordance with one aspect, the load-bearing support structure system 1 includes a first composite structure with an electrical controller 7. The first composite structure includes a first layer of a first thermally-responsive polymer 2; one or more first heating elements 3 positioned adjacent to the first layer 2 on a first heating element side; a second layer 4 of the first thermally-responsive polymer positioned adjacent to the one or more first heating elements 3 on a second heating element side; a temperature sensor 5 communicating with at least the first layer 2 or the second layer 4 of the first thermally-responsive polymer to detect the temperature; one or more electrical connectors 6 electrically communicating with the one or more heating elements 3. The electrical controller 7 detachably connectable to at least one of the one or more electrical connectors 6 of the composite for providing an electrical current to the one or more heating elements 3 (FIG. 1).

In one embodiment, the first layer of the first thermally-responsive polymer having a first elastic modulus at a temperature below a glass transition temperature or a melting temperature and a second elastic modulus at a temperature greater than the glass transition temperature or the melting temperature, when the first elastic modulus is larger than the second elastic modulus by at least approximately 10 times to approximately 100 times. This range ensures that at the temperature of use (typically, room temperature), the polymer has sufficient rigidity that it can be used for load-bearing applications, for example, as a fixation device for body parts under orthopaedic treatment or as a holder for an object of a particular shape. At temperatures above the melting or glass transition temperature, the material becomes sufficiently soft such that it is pliable and can be easily shaped and molded to the desired contours. Examples of elastic moduli ranges may be from approximately $9 \times 10^8$ Pa to approximately $5 \times 10^9$ Pa at temperatures below the glass transition temperature or melting temperature, and from approximately $1 \times 10^6$ to approximately $5 \times 10^7$ Pa at temperatures above the glass transition temperature or melting temperature. Other ranges may also be suitable as long as there is a large difference in mechanical properties below and above the glass transition temperature or melting temperature. In another embodiment, the first thermally-responsive polymer layer is selected from a polyurethane block co-polymer, polylactic acid, polystyrene or polyacrylate. In one embodiment, the first thermally-responsive polymer layer includes a thermally conductive filler in an amount up to 85 weight %, where the thermally-conductive filler is selected from one or more of boron nitride (BN), silica coated aluminum nitride (SCAN), metal oxides, $SiO_2$, or non-oxide ceramic powders. In one embodiment, the one or more first heating elements selected from one or more of carbon fibers, carbon fabric, conductive inks, metal mesh, metal film, metal wires, or flexible printed circuits.

In one embodiment, the second layer having a first elastic modulus at a temperature below a glass transition temperature or a melting temperature and a second elastic modulus at a temperature greater than the glass transition temperature or the melting temperature, when the first elastic modulus is larger than the second elastic modulus by at least approximately 10 to approximately 100 times. The second thermally-responsive polymer layer is selected from polyurethane block co-polymer, polylactic acid, polystyrene or polyacrylate.

In one embodiment, the electronically-activated, self-molding and re-shapeable load-bearing support structure system further includes one or more second heating elements positioned between the first layer and the second layer of the first thermally-responsive polymer, the one or more second heating elements selected from one or more of carbon fibers, carbon fabric, conductive inks, metal mesh, metal film, metal wires, or flexible printed circuits.

In one embodiment, the composite structure further comprises a third layer of a second thermally-responsive polymer laterally adjacent to the first layer of the first thermally-responsive polymer having a third elastic modulus at a temperature below a glass transition temperature or a melting temperature and a fourth elastic modulus at a temperature greater than the glass transition temperature or the melting temperature, when the third elastic modulus is larger than the fourth elastic modulus by at least approximately 10 to approximately 100 times, where the third layer of a second thermally-responsive polymer has a third elastic modulus that is greater than the first elastic modulus of the first thermally responsive polymer by at least approximately 10 to approximately 100 times; one or more third heating elements positioned adjacent to the third layer on a first heating element side, the one or more third heating elements selected from one or more of carbon fibers, carbon fabric, conductive inks, metal mesh, metal film, metal wires, or flexible printed circuits.

In one embodiment, a fourth layer of the second thermally-responsive polymer positioned adjacent to the one or more third heating elements on a third heating element side, the fourth layer having a third elastic modulus at a temperature below a glass transition temperature or a melting temperature and a fourth elastic modulus at a temperature greater than the glass transition temperature or the melting temperature, when the third elastic modulus is larger than the fourth elastic modulus by at least approximately 10 to approximately 100 times such that a region of the third and fourth layers of the second thermally-responsive material provides a region of greater stiffness or rigidity to the composite structure.

The electrical controller electrically communicating with the temperature sensor when the electrical controller is connected to the one or more electrical connectors and for providing electricity to the heating element, the amount of electricity being determined by a measured temperature from the temperature sensor and a predetermined set temperature above the glass transition temperature or the melting temperature. In one embodiment, the temperature sensor includes a thermocouple, a resistance temperature detector, or a thermistor. In another embodiment, the controller includes a temperature feedback control circuit 8, and it is configured to provide a temperature from 15° C. to 85° C. In another embodiment, the temperature feedback control circuit 8 is selected from a dynamic voltage control or a dynamic current control feedback circuit.

Figure 2:
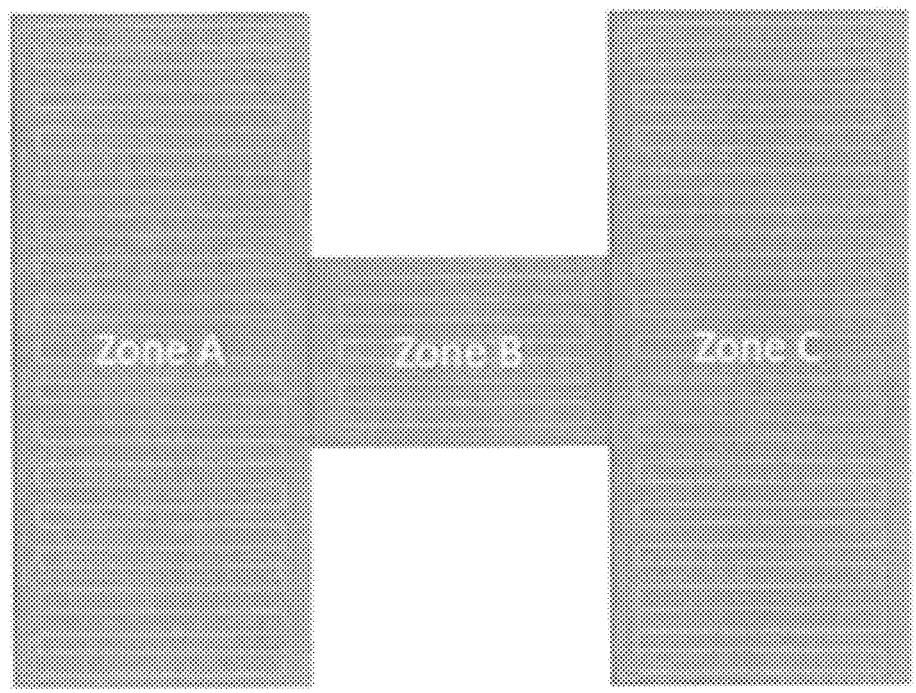
FIG. 2 depicts the three separated heating zones.

In one embodiment, the one or more first heating elements forming a first heating zone. The one or more second heating elements forming a second heating zone. The one or more third heating elements forming a third heating zone. Each heating zone can be controlled by the electrical controller independently. By controlling the different zone of the heating elements to generate heat, the hardening and softening at different zone can be controlled independently. According to difference usage of the application, separated zone to be soft or hard provides convenience in usage. For example, in the application of surgical fixation for human arm, the load-bearing support structure system can be separated into three zones as shown in FIG. 2. For the zone A and zone C will be soft first for fixing the load-bearing support structure system on the human arm. After fixation of the zone A and zone C, the zone B can be softening for turning the surgical treatment needed.

Under the configuration of electro-active fixation multi-layer composite materials, the polymer layer possessing Tg or Tm in the range between room temperature and 85° C. provides high stiffness when temperature is higher than Tg or Tm and low stiffness when temperature is lower than Tg or Tm. The modulus change is not less than one order of magnitude when temperature changes across Tg or Tm. Sandwiched heating layer inside is used to control the temperature by electrical joule effect.

Figure 3:
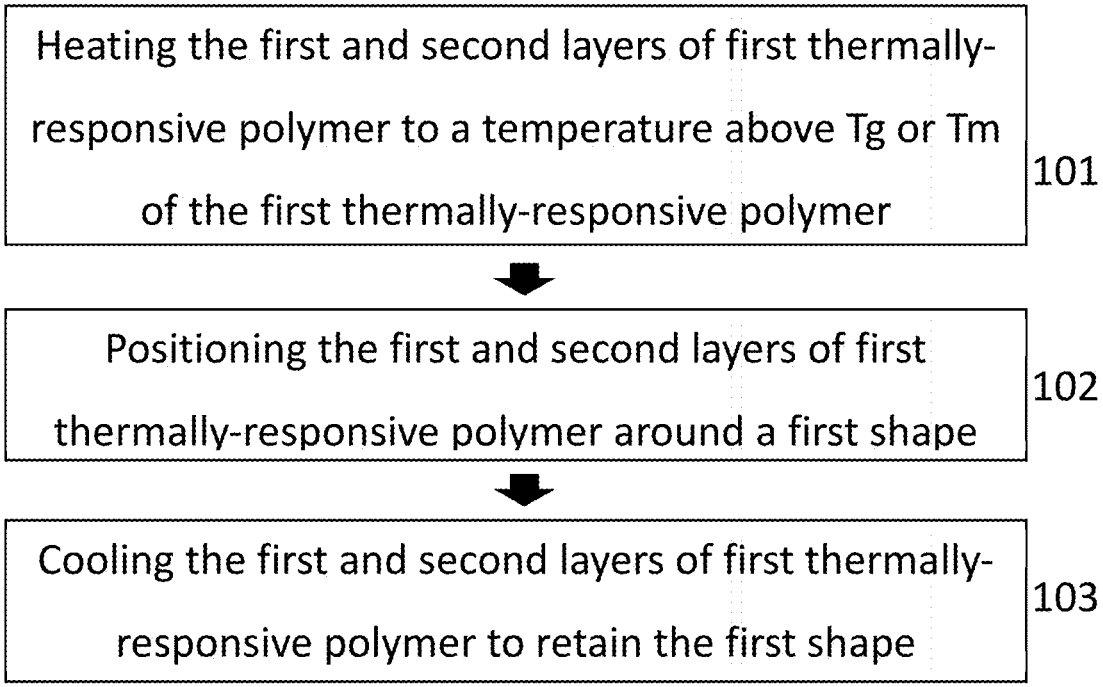
FIG. 3 depicts a flow chat of molding the load-bearing support structure system in accordance with one embodiment of the present invention.

A novel method for molding the electronically-activated, self-molding and re-shapeable load-bearing support structure system is provided. FIG. 3 illustrates one embodiment of the present method. In step 101, the first and second layers of first thermally-responsive polymer are heated to a temperature above a glass transition temperature (Tg) or a melting temperature (Tm) of the first thermally-responsive polymer. In step 102, the first and second layers of first thermally-responsive polymer are positioned around a first shape. In step 103, the first and second layers of first thermally-responsive polymer are cooled to retain the first shape. The shape is a human or animal body part.

Figure 4:
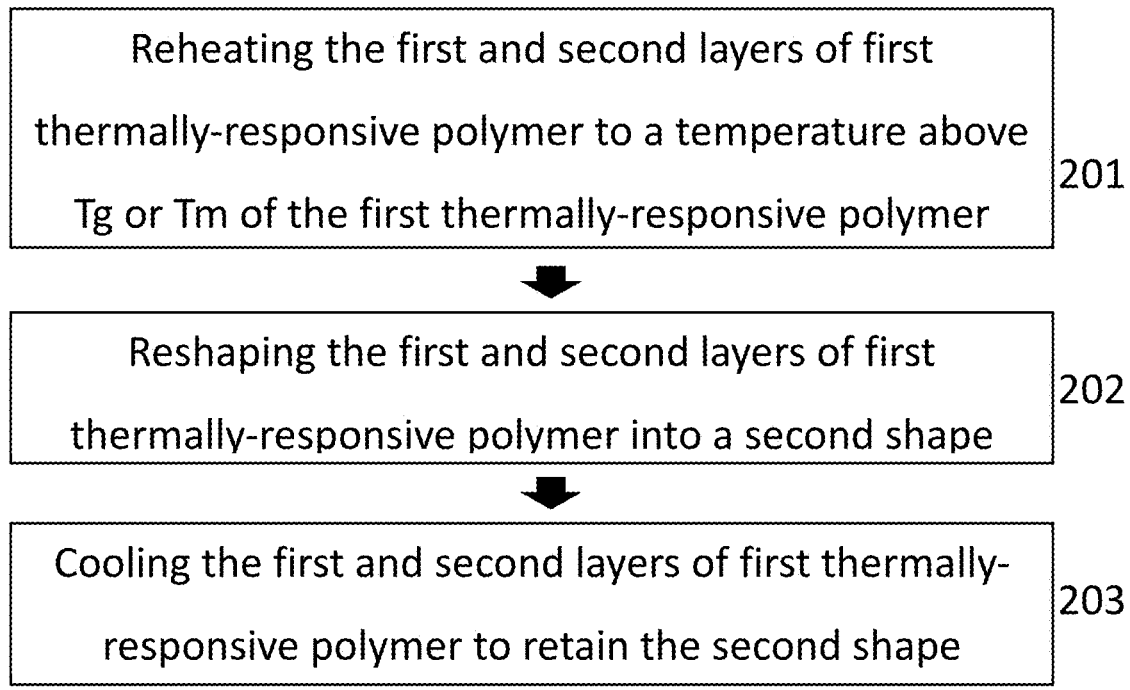
FIG. 4 depicts a flow chat of molding the load-bearing support structure system in accordance with another embodiment of the present invention.

As indicated in FIG. 4, in step 201, the method for molding the load-bearing support structure system further comprising reheating the first and second layers of first thermally-responsive polymer to a temperature above a glass transition temperature or a melting temperature of the first thermally-responsive polymer. In step 202, the first and second layers of first thermally-responsive polymer are reshaped into a second shape. In step 203, the first and second layers of first thermally-responsive polymer are cooled to retain the second shape. The shape is a human or animal body part. The second shape is different from the first shape.

The following examples are provided to illustrate the invention, which by no means are exhaustive. They are intended to be illustrative only and are not intended to limit the scope of the invention.

EXAMPLES

Example 1

Figure 5:
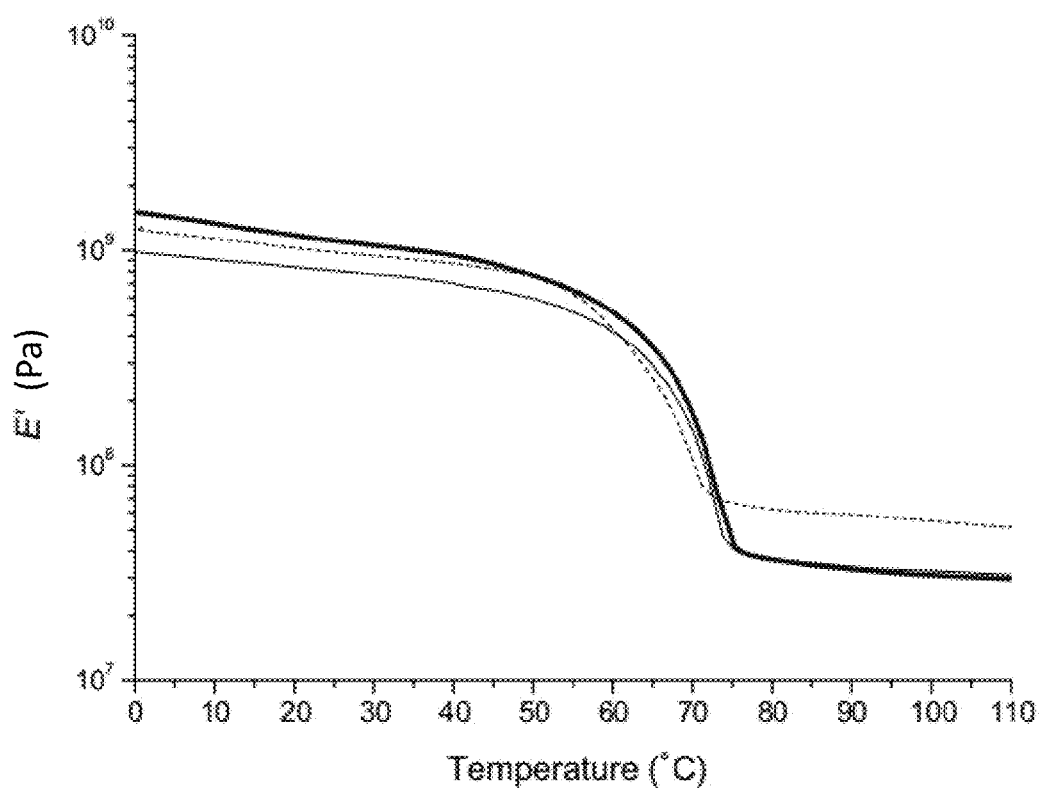
FIG. 5 is a plot of elastic modulus vs. temperature for several materials.

One of polymer candidates can be Polycaprolactone diol (Mn=10000) based SMP with MDI(4,4'-Methylenebis(phenylisocyanate)), BDO(1,4-Butanediol) in hard segments is used in SMP part as reported in literature (Zhu, Y., Hu, J., & Yeung, K. (2009). Effect of soft segment crystallization and hard segment physical crosslink on shape memory function in antibacterial segmented polyurethane ionomers. (Acta Biomaterialia, 5(9), 3346.). The Tm of soft segments of SMP used is 65° C. The elastic modulus of this polymer at temperatures below the Tm ranges from between approximately $1\times10^9$ Pa and $3\times10^9$ Pa, with the variation in the elastic modulus depending upon the amount of crystallization, molecular weight, and variation in composition of the polymer. The elastic modulus of this polymer at temperatures above the Tm ranges from between approximately $2\times10^7$ MPa and $4\times10^7$ MPa. Several curves showing the change in the elastic modulus with temperature for this class of materials is depicted in FIG. 5 with the three curves showing the differences in mechanical properties for various samples.

Example 2

One of polymer candidates can be polylactide acid such as Naturework PLA4032D® with Tg of 60° C.

Example 3

Polymer from example 2 is extruded to make sheet and then laminated with heating layer such copper mesh with thickness of 50 micros to prepare the electro-active fixation multi-layer composite materials. Electricity to heating layer generates joule heat to soften polymer layer to get deformability such as bending or rolling by hand. Air cooling without electricity power supply will increase the stiffness, which is arising from intrinsic polymer properties of glass status.

The invention claimed is:

1. An electronically-activated, self-molding and re-shapeable load-bearing support structure system comprising:
    a first composite structure including:
        a first layer of a first thermally-responsive polymer having a first elastic modulus at a temperature below a glass transition temperature or a melting temperature and a second elastic modulus at a temperature greater than the glass transition temperature or the melting temperature, when the first elastic modulus is larger than the second elastic modulus by at least approximately 10 times larger to approximately 100 times larger;
        one or more first heating elements positioned adjacent to the first layer on a first heating element side, the one or more first heating elements selected from one or more of carbon fibers, carbon fabric, conductive inks, metal mesh, metal film, metal wires, or flexible printed circuits, the one or more first heating elements forming a first heating zone;
        a second layer of the first thermally-responsive polymer positioned adjacent to the one or more first heating elements on a second heating element side, the second layer having a first elastic modulus at a temperature below a glass transition temperature or a melting temperature and a second elastic modulus at a temperature greater than the glass transition temperature or the melting temperature, when the first elastic modulus is larger than the second elastic modulus by at least approximately 10 times larger to approximately 100 times larger;
        a temperature sensor communicating with at least the first layer or the second layer of the first thermally-responsive polymer;
        one or more electrical connectors electrically communicating with the one or more heating elements;
    an electrical controller detachably connectable to at least one of the one or more electrical connectors of the composite for providing an electrical current to the one or more heating elements, the electrical controller electrically communicating with the temperature sensor when the electrical controller is connected to the one or more electrical connectors and for providing electricity to the heating element, the amount of electricity being determined by a measured temperature from the temperature sensor and a predetermined set temperature above the glass transition temperature or the melting temperature.

2. The electronically-activated, self-molding and re-shapeable load-bearing support structure system according to claim 1, further comprising one or more second heating elements positioned between the first layer and the second layer of the first thermally-responsive polymer, the one or more second heating elements selected from one or more of carbon fibers, carbon fabric, conductive inks, metal mesh, metal film, metal wires, or flexible printed circuits, the one or more second heating elements forming a second heating zone, the second heating zone being independently controllable by the controller from the first heating zone.

3. The electronically-activated, self-molding and re-shapeable load-bearing support structure system according to claim 1, wherein the composite structure further comprises a third layer of a second thermally-responsive polymer laterally adjacent to the first layer of the first thermally-responsive polymer having a third elastic modulus at a temperature below a glass transition temperature or a melting temperature and a fourth elastic modulus at a temperature greater than the glass transition temperature or the melting temperature, when the third elastic modulus is larger than the fourth elastic modulus by at least approximately 10 times larger to approximately 100 times larger and wherein the third layer of a second thermally-responsive polymer has a third elastic modulus that is greater than the first elastic modulus of the first thermally responsive polymer by at least approximately 10 times larger to approximately 100 times larger;
one or more third heating elements positioned adjacent to the third layer on a first heating element side, the one or more third heating elements selected from one or more of carbon fibers, carbon fabric, conductive inks, metal mesh, metal film, metal wires, or flexible printed circuits, the one or more third heating elements forming a third heating zone;
a fourth layer of the second thermally-responsive polymer positioned adjacent to the one or more third heating elements on a third heating element side, the fourth layer having a third elastic modulus at a temperature below a glass transition temperature or a melting temperature and a fourth elastic modulus at a temperature greater than the glass transition temperature or the melting temperature, when the third elastic modulus is larger than the fourth elastic modulus by at least approximately 10 times larger to approximately 100 times larger such that a region of the third and fourth layers of the second thermally-responsive material provides a region of greater stiffness or rigidity to the composite structure.

4. The electronically-activated, self-molding and re-shapeable load-bearing support structure system according to claim 3, wherein the second thermally-responsive polymer layer is selected from polyurethane block co-polymer, polylactic acid, polystyrene or polyacrylate.

5. The electronically-activated, self-molding and re-shapeable load-bearing support structure system according to claim 1, wherein the temperature sensor includes a thermocouple, a resistance temperature detector, or a thermistor.

6. The electronically-activated, self-molding and re-shapeable load-bearing support structure system according to claim 1, wherein the controller is configured to provide a temperature from 15° C. to 85° C.

7. The electronically-activated, self-molding and re-shapeable load-bearing support structure system according to claim 1, wherein the controller includes a temperature feedback control circuit.

8. The electronically-activated, self-molding and re-shapeable load-bearing support structure system according to claim 7, wherein the temperature feedback control circuit is selected from a dynamic voltage control or a dynamic current control feedback circuit.

9. The electronically-activated, self-molding and re-shapeable load-bearing support structure system according to claim 1, wherein the controller includes a feedback control circuit.

10. The electronically-activated, self-molding and re-shapeable load-bearing support structure system according to claim 1 wherein the first thermally-responsive polymer layer includes a thermally conductive filler in an amount up to 85 weight %.

11. The electronically-activated, self-molding and re-shapeable load-bearing support structure system according to claim 10, wherein the thermally-conductive filler is selected from one or more of boron nitride (BN), silica coated aluminum nitride (SCAN), metal oxides, $SiO_2$, or non-oxide ceramic powders.

12. The electronically-activated, self-molding and re-shapeable load-bearing support structure system according to claim 1, wherein the first thermally-responsive polymer layer is selected from a polyurethane block co-polymer, polylactic acid, polystyrene or polyacrylate.

13. The electronically-activated, self-molding and re-shapeable load-bearing support structure system according to claim 1 wherein the elastic modulus of the first thermally-responsive polymer is between approximately $9\times10^8$ Pa to approximately $5\times10^9$ Pa at temperatures below the glass transition temperature or the melting temperature, and is from approximately $1\times10^6$ Pa to approximately $5\times10^7$ Pa at temperatures above the glass transition temperature or the melting temperature.

14. A method of molding the electronically-activated, self-molding and re-shapeable load-bearing support structure system according to claim 1, comprising:
heating the first and second layers of first thermally-responsive polymer to a temperature above a glass transition temperature or a melting temperature of the first thermally-responsive polymer;
positioning the first and second layers of first thermally-responsive polymer around a first shape;
cooling the first and second layers of first thermally-responsive polymer to retain the first shape.

15. The method of molding according to claim 14, wherein the shape is a human or animal body part.

16. The method of molding according to claim 14, further comprising:
reheating the first and second layers of first thermally-responsive polymer to a temperature above a glass transition temperature or a melting temperature of the first thermally-responsive polymer;
reshaping the first and second layers of first thermally-responsive polymer into a second shape;
cooling the first and second layers of first thermally-responsive polymer to retain the second shape.

17. The method of molding according to claim 16, wherein the second shape is different from the first shape.

* * * * *